(12) United States Patent
Albert et al.

(10) Patent No.: US 7,399,771 B2
(45) Date of Patent: *Jul. 15, 2008

(54) PIPERIDINE DERIVATIVES AS CCR5 INHIBITORS

(75) Inventors: Rainer Albert, Basel (CH); Nigel Graham Cooke, Oberwil (CH); Gebhard Thoma, Lörrach (DE); Christian Bruns, Freiburg (DE); François Nuninger, Wittenheim (FR); Markus Streiff, Birsfelden (CH); Hans-Günter Zerwes, Lörrach (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/529,776

(22) PCT Filed: Oct. 6, 2003

(86) PCT No.: PCT/EP03/11035

§ 371 (c)(1),
(2), (4) Date: May 5, 2005

(87) PCT Pub. No.: WO2004/031172

PCT Pub. Date: Apr. 15, 2004

(65) Prior Publication Data

US 2006/0004047 A1    Jan. 5, 2006

(30) Foreign Application Priority Data

Oct. 7, 2002   (GB) .................................. 0223223.9

(51) Int. Cl.
*A61K 31/445* (2006.01)
*C07D 401/14* (2006.01)

(52) U.S. Cl. ................. 514/316; 546/186; 546/188

(58) Field of Classification Search ............. 546/186, 546/188; 514/316
See application file for complete search history.

(56) References Cited

U.S. PATENT DOCUMENTS

2004/0142920 A1* 7/2004 Albert et al. ............. 514/217

FOREIGN PATENT DOCUMENTS

| WO | WO9801425 A1 * | 1/1998 |
| WO | 00/66559 | 11/2000 |
| WO | WO0066559 A1 * | 11/2000 |
| WO | 02/081449 | 10/2002 |
| WO | WO02081449 A1 * | 10/2002 |
| WO | 03/020716 | 3/2003 |

OTHER PUBLICATIONS

: http://www.bakerbotts.com/infocenter/publications/detail.aspx?id=bffe4a7d-5beb-4cf8-a189-15a5f190f0eb).*
http://www.dorsey.com/publications/legal_detail.aspx?FlashNavID=pubs_legal&pubid=170565003).*
Cohen et al., Am. J. Clin. Pathol., 1996, 105, 589.*
Assigment WO 02/081449, U.S. Appl. No. 10/472,653.*
Thom et al. "Orally bioavailable . . . " J. Med. Chem. 47, p. 1939-55 (2004).*
Jewell et al. "Susceptibility . . . " CA 134:250801 (2001).*
Youhua et al. "Clinical study of . . . " Transplatation Proceedings v.32 p. 1704 (2000).*
Palani et al., "Discovery of 4-[(Z)-(4-Bromophenyl)-(ethoxyimino)methyl]-1'-[(2,4-dimethyl-3-pyridinyl)carbonyl]-4'-methyl-1,4'-bipiperidine N-Oxide (SCH 351125): An Orally Bioavailable Human CCR5 Antagonist for the treatment of HIV Infection", J. Med. Chem., vol. 44, No. 21, pp. 3339-3342 (2001).

* cited by examiner

*Primary Examiner*—Celia Chang
(74) *Attorney, Agent, or Firm*—Novartis AG

(57) ABSTRACT

Disclosed are compounds of formula I:

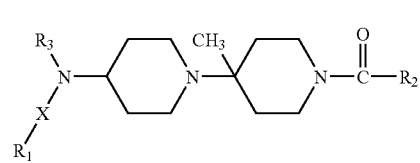

wherein $R_1$, $R_2$, $R_3$ and X are as defined herein, in free or salt form, which are useful as CCR5 inhibitors, e.g. in the prevention or treatment of disorders mediated by interactions between chemokine receptors and their ligands.

3 Claims, No Drawings

PIPERIDINE DERIVATIVES AS CCR5 INHIBITORS

The present invention relates to piperidine derivatives, process for their production, their uses and pharmaceutical compositions containing them.

More particularly, the present invention provides a compound of formula I

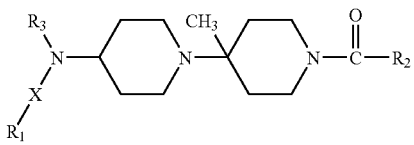

wherein
1) $R_2$ is a residue of formula

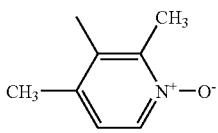

and
a) $R_1$ is thienyl, furyl, thiazolyl or 2-methyl-thiazolyl,
   X is —CH$_2$—, and
   $R_3$ is benzo[1,3]dioxol-yl or phenyl optionally mono-substituted by halogen,
   or
b) $R_1$ is phenyl substituted by —O$_2$CH$_3$ or CN
   X is —CH$_2$—, and
   $R_3$ is phenyl
   or
c) $R_1$ is phenyl
   X is a direct bond, and
   $R_3$ is pyridyl,
   or
2) $R_2$ is a residue of formula

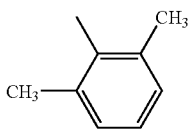

and
a) $R_1$ is pyridyl, phenyl optionally substituted by carboxy or C$_{1-4}$alkoxycarbonyl
   2-methylthiazolyl, indolyl or benzimidazol-2-yl,
   X is —CH$_2$— or —CH$_2$CH$_2$—, and
   $R_3$ is phenyl optionally substituted by Hal,
   or
b) $R_1$ is phenyl
   X is a direct bond
   $R_3$ is pyridyl,
   or
c) $R_1$ is 2-methyl-thiazolyl,
   X is —CH$_2$—, and
   $R_3$ is 1-methyl-indolyl
   or 3) $R_2$ is a residue of formula

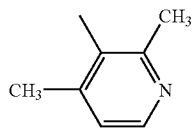

and
a) $R_1$ is 2-methyl-thiazolyl
   X is —CH$_2$—, and
   $R_3$ is phenyl substituted by halogen
   or
b) $R_1$ is pyridyl
   X is a direct bond, and
   $R_3$ is phenyl
   or
4) $R_2$ is a residue of formula

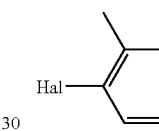 or 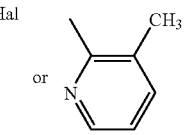 or 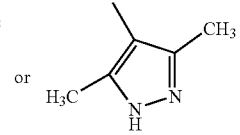

wherein
Hal is F or Cl,
Z is —C= or —N=
and
a) $R_1$ is phenyl, X is a direct bond and $R_3$ is pyridyl or
b) $R_1$ is pyridyl, X is a direct bond and $R_3$ is phenyl or
5) $R_2$ is a residue of formula

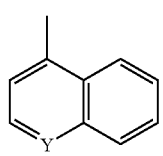

wherein Y is —C= or —N=
and
$R_1$ is pyridyl, X is a direct bond and $R_3$ is phenyl, or
6) $R_2$ is a residue of formula

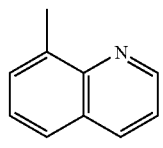

X is a direct bond and one of $R_1$ and $R_3$ is phenyl and the other is pyridyl,
or 7) $R_2$ is a residue of formula

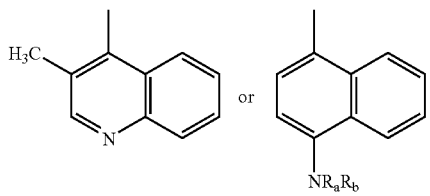

wherein each of $R^a$ and $R^b$, independently, is H, $CH_3$ or $C_2H_5$, $R_1$ and $R_3$ are phenyl,
and X is a direct bond
or
8) $R_2$ is a residue of formula

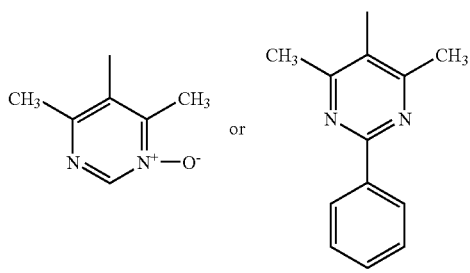

$R_1$ is pyridyl, X is a direct bond and $R_3$ is phenyl,
or
9) $R_2$ is indol-4-yl, $R_1$ is pyridyl, X is a direct bond and $R_3$ is phenyl, in free form or in salt form.

Halogen is F, Cl, Br or I. Phenyl monosubstituted by halogen is preferably para substituted.

When phenyl is substituted by carboxy or $C_{1-4}$alkoxycarbonyl, it is preferably in position meta. Indolyl is preferably 3-indolyl.

The compounds of formula I may exist in free form or in salt form, e.g. addition salts with e.g. organic or inorganic acids, for example, hydrochloric acid, acetic acid when e.g. $R_1$, $R_2$, and/or $R_3$ comprises an optionally substituted amino group or a heterocyclic residue which can form addition salts. The compounds of formula I have one or more asymmetric centers in the molecule, and the present invention is to be understood as embracing the various optical isomers, as well as racemates, diastereoisomers and mixtures thereof.

The present invention also includes a process for the preparation of a compound of formula I which process comprises
a) amidating a compound of formula II

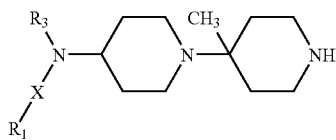

wherein $R_1$, $R_3$ and X are as indicated above
with a compound of formula III $R_2$—CO—A       III wherein $R_2$ is as defined above, A is a leaving group, e.g. Cl or Br; or b) reacting a compound of formula IV

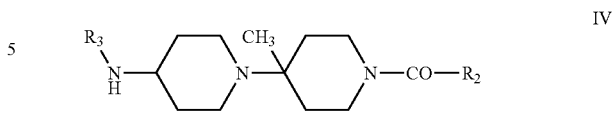

wherein $R_2$ and $R_3$ are as defined above, with a compound of formula V $R_1$—X-Hal       V wherein $R_1$ and X are as defined above;

and, where required, converting the resulting compound of formula I obtained in free form into the desired salt form, or vice versa.

The reaction steps a) or b) may be performed in accordance with methods known in the art or as disclosed in the Examples below.

Compounds of formula II, used as starting material may be prepared as follows:

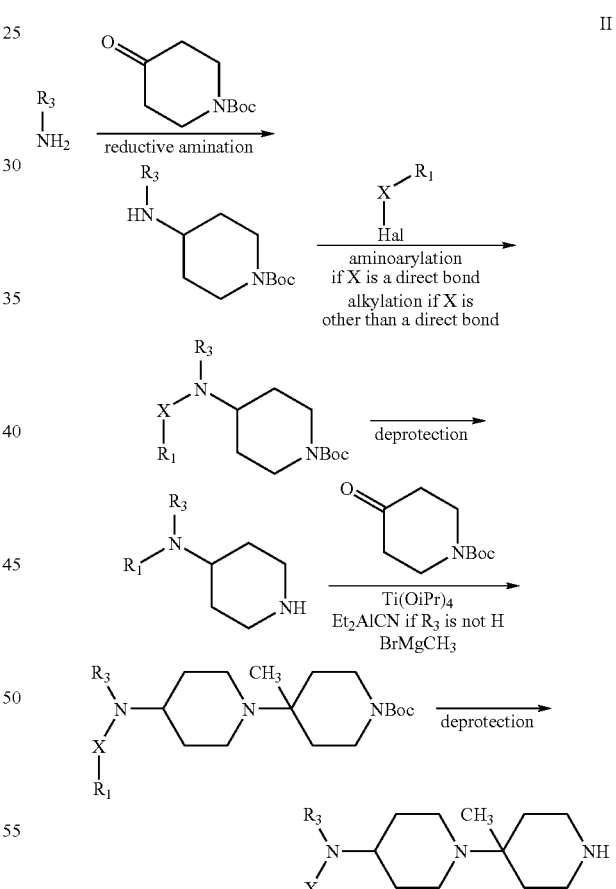

wherein X, $R_1$ and $R_3$ are as defined above and Hal is Cl, Br or I. In above formulae, Boc is a protecting group which means tert-butyloxycarbonyl. This protecting group may be replaced in above reaction scheme by any amino protecting group, e.g. as disclosed in "Protective Groups in Organic Synthesis" by T. W. Greene, J. Wiley & Sons NY, $2^{nd}$ ed., Chapter 7, 1991 and references therein, e.g. benzyloxycarbonyl or 9-fluorenylmethoxy carbonyl.

Alternatively, compounds of formula II may be prepared as follows:

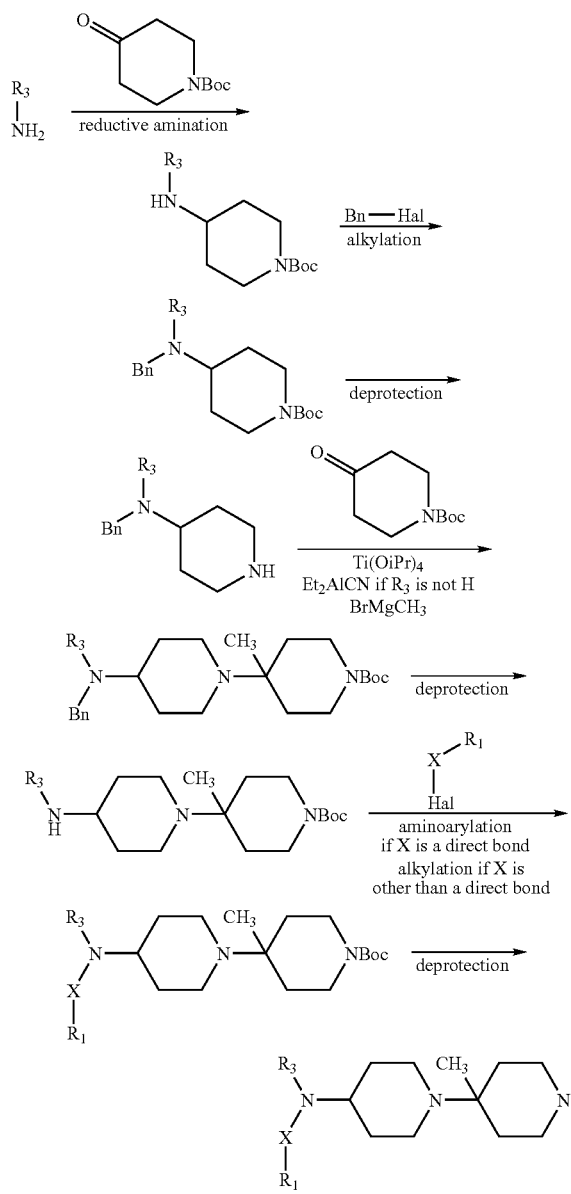

wherein $R_1$, $R_3$, X and Hal are as herein defined and Bn is benzyl.

Compounds of formula IV, used as starting material, may be prepared as follows:

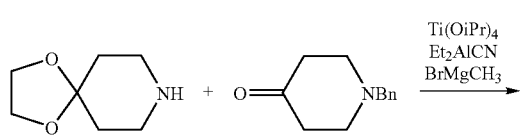

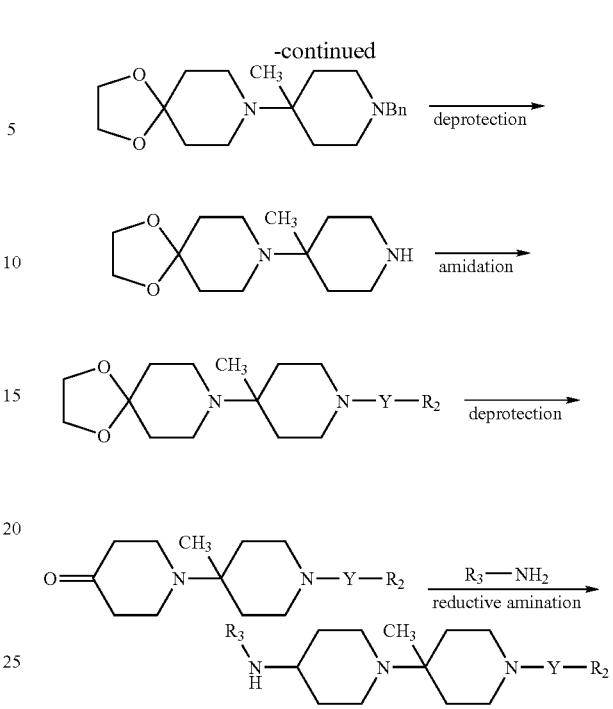

wherein $R_2$, $R_3$, Y and Bn are as defined above.

Above reactions may be carried out in accordance with methods known in the art or as disclosed hereafter.

Insofar as the production of the starting materials is not particularly described, the compounds are known or may be prepared analogously to methods known in the art or as described hereafter.

The following Examples are illustrative of the invention, without limitation.

EXAMPLE 1

(2,4-Dimethyl-pyridin-3-yl)-[4'-methyl-4-phenyl-pyridin-3-yl-amino)-[1,4']bipiperidinyl-1'-yl]-methanone

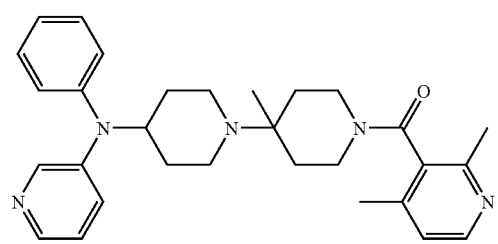

It is prepared from (4'-methyl-[1,4']bipiperidinyl-4-yl)-phenyl-pyridin-3-yl-amine and 2,4-dimethyl-nicotinic acid using a procedure as described for Example 1 of International patent application PCT/EP02/03871 MS/ESI 484 [M+H]$^+$. (4'-Methyl-[1,4']bipiperidinyl-4-yl)-phenyl-pyridin-3-yl-amine used as starting material can be prepared from tert-Butyl 4-phenylaminopiperidine-1-carboxylate and 3-bromopyridine using procedures as described in Example 1a-1d of PCT/EP02/03871. MS/ESI 351 [M+H]$^+$ By following the procedure as disclosed in example 1, the compounds of formula $X_1$

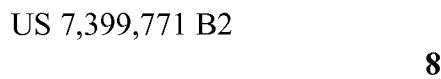

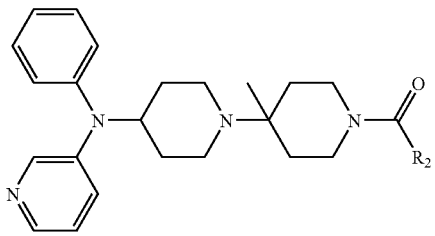

wherein R₂ has the significances as indicated in Table 1, may be prepared.

TABLE 1

| Example | R₂ | MS/ESI (M + H)⁺ |
|---|---|---|
| 2 | pyrimidine with CH₃, CH₃, phenyl substituents | 561 |
| 3 | naphthyl | 505 |
| 4 | 2,6-dichlorophenyl | 523/525 |
| 5 | quinolin-4-yl | 506 |
| 6 | quinolin-8-yl | 506 |
| 7 | dimethyl pyridine N-oxide | 501 |
| 8 | 2,6-difluorophenyl | 491 |
| 9 | 3-methylpyridin-2-yl | 470 |
| 10 | 3,5-dichloropyridin-4-yl | 525 |
| 11 | 3,5-dimethyl-1H-pyrazol-4-yl | 473 |

EXAMPLE 12

(2,4-Dimethyl-1-oxy-pyridin-3-yl)-[4'-methyl-4-(phenyl-pyridin-2-yl-amino)-[1,4']bipiperidinyl-1'-yl]methanone

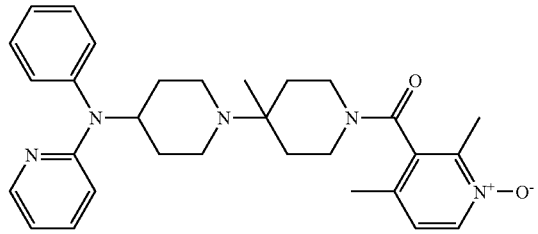

Is prepared from (4'-methyl-[1,4']bipiperidinyl-4-yl)-phenyl-pyridin-2-yl-amine and 2,4-dimethyl-1-oxy-nicotinic acid acid using a procedure as described for Example 1 above. MS/ESI 500 [M+H]⁺.

(4'-Methyl-[1,4']bipiperidinyl-4-yl)-phenyl-pyridin-2-yl-amine used as starting material can be prepared form tert-butyl 4-(phenyl-pyridin-2-ylamino)piperidine-1-carboxylate using a procedure as described Example 1b-1d of PCT/EP02/03871. MS/ESI 351 [M+H]⁺.

tert-Butyl 4-(phenyl-pyridin-2-ylamino)piperidine-1-carboxylate may be prepared as follows:

A mixture of tert-Butyl 4-phenylamino-piperidine-1-carboxylate (0.8 g; 3 mmol), 2-bromopyridine (0.3 ml; 3 mmol), tris(dibenzylideneacetone)-di-palladium (0) (0.27 g, 0.3 mmol), 9,9-dimethyl-bi(diphenylphosphine)xanthene (0.26 g, 0.45 mmol) and potassium tert-butoxide (3 ml, 1 mol solution in THF) in toluene (30 ml) is heated to 110° C. for 15 h. The cooled mixture is filtered and the filtrate is diluted with ethyl acetate. The filtrate is washed with sodium hydrogen carbonate and brine and dried with sodium sulfate. The solvent is removed and the residue is recrystallized from acetonitrile to afford the title compound as a brown solid. MS/ESI 354 [M+H]$^+$

EXAMPLE 13

(2,6-Dimethyl-phenyl)-[4'-methyl-4-(phenyl-pyridin-4-yl-amino)-[1,4']bipiperidinyl-1'-yl]-methanone

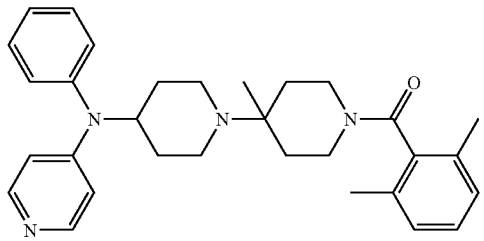

It is prepared from (4'-methyl-[1,4']bipiperidinyl-4-yl)-phenyl-pyridin-4-yl-amine and 2,6-dimethyl-benzoic acid using a procedure as described in above Example 1. MS/ESI 483 [M+H]$^+$. (4'-Methyl-[1,4']bipiperidinyl-4-yl)-phenyl-pyridin-4-yl-amine used as starting material can be prepared from tert-butyl 4-phenylaminopiperidine-1-carboxylate and 4-bromopyridine hydrochloride using procedures as described in Example 1a-1d of PCT/EP02/03871. MS/ESI 351 [M+H]$^+$ By following the procedure as disclosed in example 13, the compounds of formula $X_2$

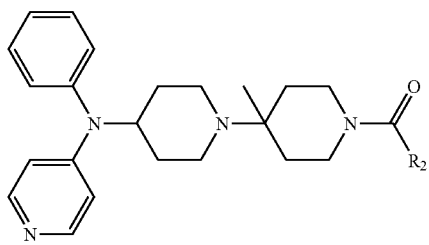

$X_2$ wherein $R_2$ has the significances as indicated in Table 2, may be prepared.

TABLE 2

| Example | $R_2$ | MS/ESI (M + H)$^+$ |
|---|---|---|
| 14 | (2,6-difluorophenyl) | 491 |

TABLE 2-continued

| Example | $R_2$ | MS/ESI (M + H)$^+$ |
|---|---|---|
| 15 | (quinolin-8-yl) | 506 |
| 16 | (2,6-dichlorophenyl) | 523/525 |
| 17 | (1H-indol-4-yl) | 494 |
| 18 | (2,4-dimethylpyridine N-oxide) | 500 |
| 19 | (naphthalen-1-yl) | 505 |

EXAMPLE 20

(4-Dimethylamino-naphthalen-1-yl)-(4-diphenylamino-4'-methyl-[1,4']bipiperidinyl-1'-yl-methanone

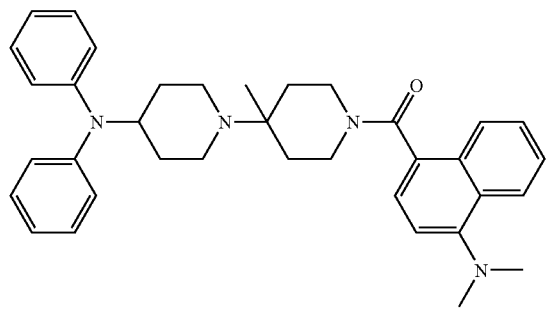

It is prepared from (4'-methyl-[1,4']bipiperidinyl-4-yl)-diphenyl-amine and 4-Dimethylamino-naphthalene-1-carboxylic acid using a procedure as described in above Example 1. MS/ESI 547 [M+H]$^+$. 4'-Methyl-[1,4']bipiperidinyl-4-yl)-diphenyl-amine used as starting material may be prepared using a procedure as described in Example 1a-1d of PCT/EP02/03871. MS/ESI 350 [M+H]$^+$

EXAMPLE 21

By following the procedure as disclosed in example 20, the compound of formula

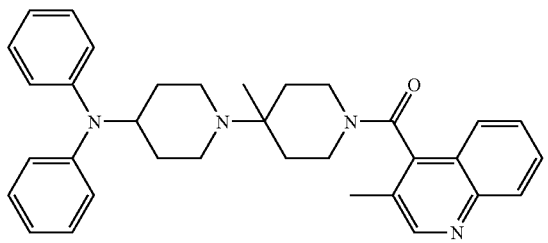

may be prepared. MS/ESI (M+H)+ 519

EXAMPLE 22

4-({[1'-(2,6-Dimethyl-benzoyl)-4'-methyl-[1,4']bipiperidinyl-4-yl]-phenyl-amino}-methyl)-benzoic acid methyl ester

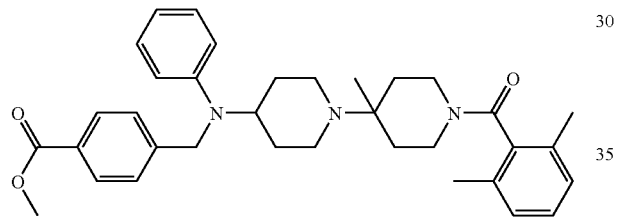

It is prepared from (2,6-dimethyl-phenyl)-(4'-methyl-4-phenylamino-[1,4']-bipiperidinyl-1'-yl)-methanone and 4-bromomethyl-benzoic acid methyl ester using a procedure as described for Example 52 of PCT/EP02/03871. MS/ESI 554 [M+H]+. (2,6-Dimethyl-phenyl)-(4'-methyl-4-phenylamino-[1,4']bipiperidinyl-1'-yl)-methanone used as starting material may be prepared using a procedure similar to that described in Example 51a-e of PCT/EP02/03871. MS/ESI 406 [M+H]+

By following the procedure as disclosed in example 22, the compounds of formula $X_3$

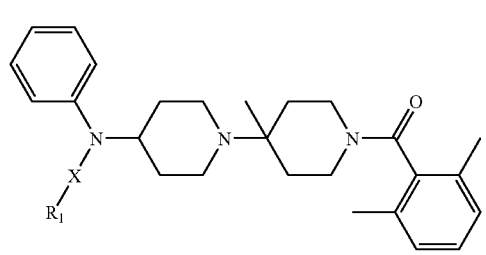

wherein —X—$R_1$ has the significances as indicated in Table 3, may be prepared.

TABLE 3

| Example | X—$R_1$ | MS/ESI (M + H)+ |
|---|---|---|
| 23 | benzoic acid methyl ester (methylene-linked) | 554 |
| 24 | pyridin-3-ylmethyl | 497 |
| 25 | benzoxazol-2-ylmethyl (2-hydroxy form) | 536 |
| 26 | phenylpropyl | 510 |
| 27 | indol-3-ylethyl | 549 |

EXAMPLE 28

4-({[1'-(2,6-Dimethyl-benzoyl)-4'-methyl-[1,4']bipiperidinyl-yl]-phenyl-amino}-methyl)-benzoic acid

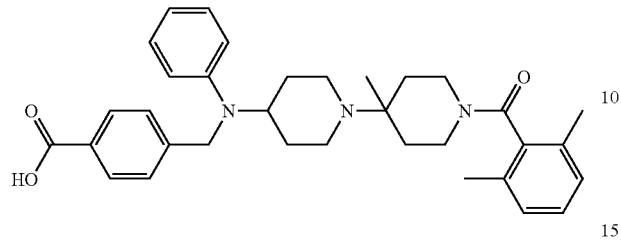

A mixture of 4-({[1'-(2,6-Dimethyl-benzoyl)-4'-methyl-[1,4']bipiperidinyl-4-yl]-phenyl-amino}-methyl)-benzoic acid methyl ester (180 mg, 0.325 mmol), methanol (10 ml), water (3 ml) and 33 mmol) was heated under reflux for 2 h. The pH was adjusted LiOH (200 mg to 1 with 2 N HCl and then to pH 7 with NaHCO$_3$. The mixture was extracted with ethyl acetate and dried with Na$_2$SO$_4$. The solvent was evaporated and the residue crystallized from methanol/water to give 4-({[1'-(2,6-Dimethyl-benzoyl)-4'-methyl-[1,4']bipiperidinyl-4-yl]-phenyl-amino}-methyl)-benzoic acid. MS/ESI 540 [M+H]$^+$

EXAMPLE 29

By following the procedure as disclosed in Example 28, the compound of formula

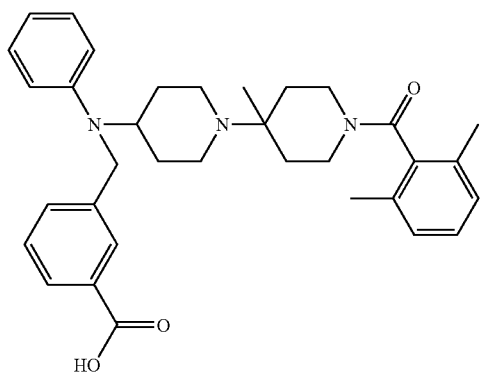

may be prepared MS/ESI (M+H)$^+$540

EXAMPLE 30

{4-[(4-Chloro-phenyl)-(2-methyl-thiazol-4-ylmethyl)-amino]4'-methyl-[1,4']bipiperidinyl-1'-yl}-(2,4-dimethyl-pyridin-3-yl)-methanone

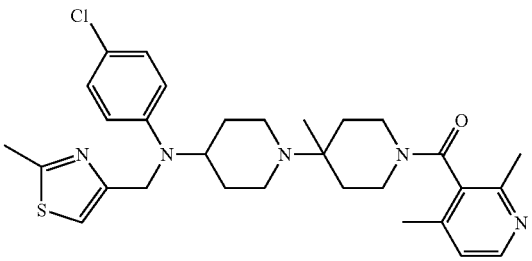

It is prepared from (chloro-phenyl)-(4'-methyl-[1,4']bipiperidinyl-4-yl-(2-methyl-thiazol-4-ylmethyl)-amine and 2,4-dimethyl-nicotinic acid using a procedure as described in Example 1 of PCT/EP02/03871. MS-ESI 552 [M+H]$^+$. (4'-Methyl-[1,4']bipiperidinyl-4-yl)-phenyl-pyridin-3-yl-amine used as starting material can be prepared from 4-chlorophenylamine, 4-oxo-piperidine-1-carboxylic acid tert-butyl ester and 4-chloromethyl-2-methyl-thiazole using procedures as described in Example 51e, 52, 1b, 1c and 1d of PCT/EP02/03871. MS/ESI 419 [M+H]$^+$ By following the procedure as disclosed in Example 30, and by using the corresponding 4-halogeno-phenylamines, the corresponding 4-chloromethyl-thiazoles and the corresponding carboxylic acids the compounds of formula X$_4$

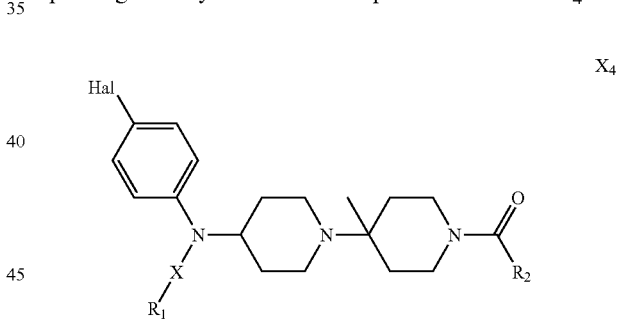

wherein X—R$_1$, R$_2$ and Hal have the significances as Indicated in Table 4, may be prepared.

TABLE 4

| Example | X—R$_1$ | R$_2$ | Hal | MS/ESI (M + H)$^+$ |
|---------|---------|-------|-----|---------------------|
| 31 | 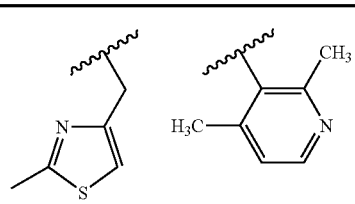 | | F | 536 |

TABLE 4-continued

| Example | X—R₁ | R₂ | Hal | MS/ESI (M + H)⁺ |
|---|---|---|---|---|
| 32 | 2-methylthiazol-4-ylmethyl | 2,3-dimethylphenyl | Cl | 551 |
| 33 | 2-methylthiazol-4-ylmethyl | 2,3-dimethylphenyl | F | 535 |
| 34 | 2-methylthiazol-4-ylmethyl | 2,4-dimethyl-1-oxy-pyridin-3-yl | Cl | 568 |
| 35 | 2-methylthiazol-4-ylmethyl | 2,4-dimethyl-1-oxy-pyridin-3-yl | F | 552 |

EXAMPLE 36

(2,4-Dimethyl-1-oxy-pyridin-3-yl)-[4'-methyl-4-(phenyl-thiophen-3-ylmethyl-amino)-[1,4']bipiperidinyl-1'-yl]-methanone

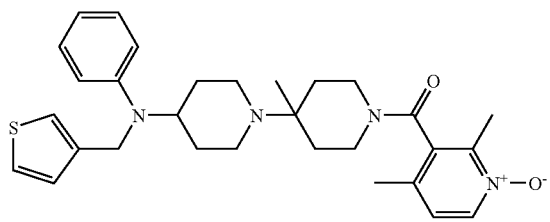

It is prepared from (4'-methyl-[1,4']bipiperidinyl-4-yl)-phenyl-thiophen-3-ylmethyl-amine and 2,4-dimethyl-1-oxy-nicotinic acid using a procedure as described in Example 1 of PCT/EP02/03871. MS/ESI 519 [M+H]⁺.

(4'-Methyl-[1,4']bipiperidinyl-4-yl)-phenyl-thiophen-3-ylmethyl-amine used as starting material may be prepared as follows:

a) 4-(Benzyl-phenyl-amino)-4'-methyl-[1,4']bipiperidinyl-1'-carboxylic acid tert-butyl ester may be obtained from benzyl-phenyl-piperidin-4-yl-amine and 4-oxo-piperidine-1-carboxylic acid tert-butyl ester using a procedure as in Example 1c of PCT/EP02/03871. MS/ESI 464 [M+H]⁺ b) 4'-Methyl-4-phenylamino-[1,4']bipiperidinyl-1'-carboxylic acid tert-butyl ester is prepared by heating a mixture of 4-(benzyl-phenyl-amino)-4'-methyl-[1,4']bipiperidinyl-1'-carboxylic acid tert-butyl ester (4.50 g, 9.70 mmol), ammonium formate (2.60 g, 41.3 mmol), Pd(OH)₂ (20% on charcoal; 1.0 g) and methanol (100 ml) for 3 h under reflux. The catalyst is filtered off and washed with ethyl acetate. The solution is washed with brine, with Na2SO4 and the solvent evaporated. MS/ESI 374 [M+H]⁺ c) 4'-Methyl-4-(phenyl-thiophen-3-ylmethyl-amino)-[1,4']bipiperidinyl-1'-carboxylic acid tert-butyl ester may be prepared from 4'-Methyl-4-phenylamino-[1,4']bipiperidinyl-1'-carboxylic acid tert-butyl ester and 3-chloromethyl-thiophene using a procedure similar to that described in Example 52 of PCT/EP02/03871. MS/ESI 470 [M+H]⁺ d) (4'-Methyl-[1,4']bipiperidinyl-4-yl)-phenyl-thiophen-3-ylmethyl-amine may be prepared from 4'-methyl-4-(phenyl-thiophen-3-ylmethyl-amino)-[1,4']bipiperidinyl-1'-carboxylic acid tert-butyl ester using a procedure similar to that described in Example 1b of PCT/EP02/03871. MS/ESI 406 [M+H]⁺

By following the procedure as disclosed in Example 36, the compounds of formula $X_5$

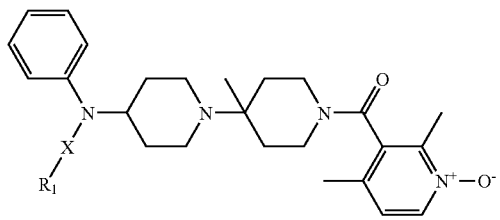

wherein $X-R_1$ has the significances as indicated in Table 5, may be prepared.

TABLE 5

| Example | X—R$_1$ | MS/ESI (M + H)$^+$ |
|---|---|---|
| 37 | 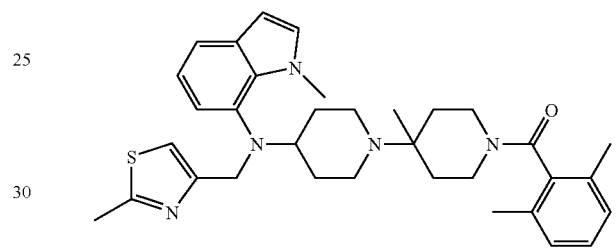 | 591 |
| 38 | | 538 |
| 39 | | 538 |
| 40 | | 503 |
| 41 | | 520 |

TABLE 5-continued

| Example | X—R$_1$ | MS/ESI (M + H)$^+$ |
|---|---|---|
| 42 | | 538 |

EXAMPLE 43

(2,6-Dimethyl-phenyl)-{4'-methyl-4[(1-methyl-1H-indol-7-yl)-(2-methyl-thiazol-4-ylmethyl)-amino]-[1,4']bipiperidinyl-1'-yl}-methanone

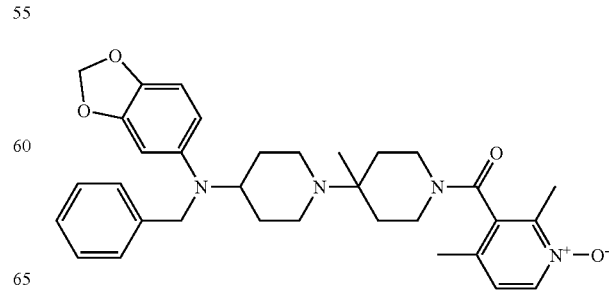

It is prepared from (2,6-dimethyl-phenyl)-[4'-methyl-4-(1-methyl-1H-indol-7-ylamino)-[1,4']bipiperidinyl-1'-yl]-methanone and 4-chloromethyl-2-methyl-thiazole using a procedure as described for Example 52 of PCT/EP02/03871. MS/ESI 570 [M+H]$^+$. (2,6-Dimethyl-phenyl)-[4'-methyl-4-(1-methyl-1H-indol-7-ylamino)-[1,4']bipiperidinyl-1'-yl]-methanone used as starting material may be prepared from 1'-(2,6-dimethyl-benzoyl)-4'-methyl-[1,4']bipiperidinyl-4-one and 1-methyl-1H-indol-7-ylamine using a procedure as described in Example 51e of PCT/EP02/03871. MS/ESI 459 [M+H]$^+$. 1'-(2,6-Dimethyl-benzoyl)-4'-methyl-[1,4']bipiperidinyl-4-one may be prepared using a procedure as described in Example 51a-d of PCT/EP02/03871. MS/ESI 329 [M+H]$^+$.

EXAMPLE 44

[4-(Benzo[1,3]dioxol-5-yl-benzyl-amino)-4'-methyl-[1,4']bipiperidinyl-1'-yl]-(2,4-dimethyl-1-oxy-pyridin-3-yl)-methanone It is prepared from benzo[1,3]dioxol-5-yl-benzyl-(4'-methyl-[1,4]bipiperidinyl-4-yl)-amine and 2,4-dimethyl-1-oxy-nicotinic acid using a procedure as described in Example 1 of PCT/EP02/03871. MS/ESI 557 [M+H]$^+$. Benzo[1,3]dioxol-5-yl-benzyl-(4'-methyl-[1,4']bipiperidinyl-4-yl)-amine used as starting material can be prepared from benzo[1,3]dioxol-5-ylamine, 4-oxo-piperidine-1-carboxylic acid tert-butyl ester and benzyl chloride using procedures as described in Examples 51e, 52, 1b, 1c and 1d of PCT/EP02/03871. MS/ESI 408 [M+H]$^+$

EXAMPLE 45

{4-[Benzo[1,3]dioxol-5-yl-(2-methyl-thiazol-4-ylmethyl)-amino]-4'-methyl-[1,4']bipiperidinyl-1'-yl}-(2,4-dimethyl-1-oxy-pyridin-3-yl)-methanone

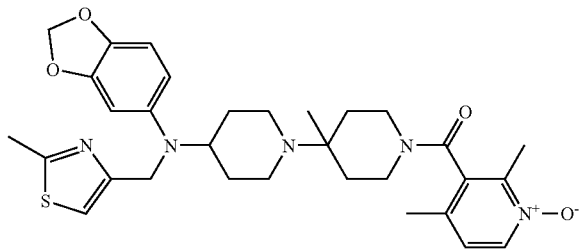

It is prepared from benzo[1,3]dioxol-5-yl-(4'-methyl-[1,4'] bipiperidinyl-4-yl)-(2-methyl-thiazol-4-ylmethyl)-amine and 2,4-dimethyl-1-oxy-nicotinic acid using a procedure as described for Example 1 of PCT/EP02/03871. MS/ESI 557 [M+H]$^+$. Benzo[1,3]dioxol-5-yl-(4'-methyl-[1,4']bipiperidinyl-4-yl)-(2-methyl-thiazol-4-ylmethyl)-amine used as starting material can be prepared from benzo[1,3]dioxol-5-ylamine, 4-oxo-piperidine-1-carboxylic acid tert-butyl ester and 4-chloromethyl-2-methyl-thiazole using procedures as described in Examples 51 e, 52, 1b, 1c and 1d of PCT/EP02/03871. MS/ESI 429 [M+H]$^+$

EXAMPLE 46

(4,6-Dimethyl-2-phenyl-pyrimidin-5-yl)-{4'-methyl-4-[(2-methyl-thiazol-4-ylmethyl)-phenyl-amino]-[1,4']bipiperidinyl-1'-yl}-methanone

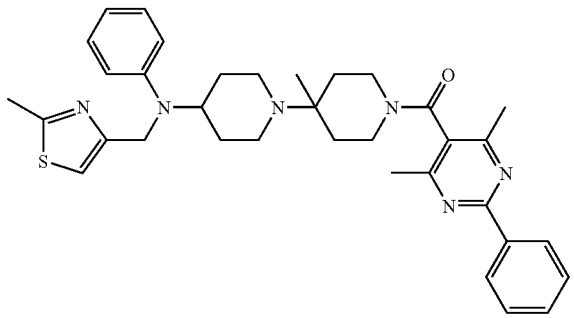

It is prepared from (4'-methyl-[1,4']bipiperidinyl-4-yl)-(2-methyl-thiazol-4-ylmethyl)-phenyl-amine and 4,6-dimethyl-2-phenyl-pyrimidine-5-carboxylic acid using a procedure as described for Example 1 of PCT/EP02/03871. MS/ESI 595 [M+H]$^+$. (4'-Methyl-[1,4']bipiperidinyl-4-yl)-(2-methyl-thiazol-4-ylmethyl)-phenyl-amine used as a starting material may be prepared using procedures described in example 83 of PCT/EP02/03871. MS/ESI 385 [M+H]$^+$ The compounds of formula I in free form or in pharmaceutically acceptable salt form exhibit valuable pharmacological properties, e.g. as CCR5 antagonists, e.g. as indicated in in vitro tests and therefore Indicated for therapy.

a) CCR5 Membrane Binding Assay

Human CCR5 is used to generate stable transfectants in CHO K1 cells. Membranes prepared from these CCR5 transfectants are used in a radioligand binding assay using 125-I MIP-1α as a ligand and the compounds of formula I are tested for inhibitory activity. The data are reported as IC$_{50}$, i.e. the concentration of compound required to achieve 50% inhibition of [I-125]MIP-1α binding. In this assay, compounds of formula I have an IC$_{50}$≦1 μM. Compounds of Examples 32 and 39 have an IC$_{50}$ of 0.5 nM, respectively.

b) CCR5 Functional Assay—Ca$^{2+}$ Mobilization

Human CCR5 is used to generate stable transfectants in CHO K1 cells. These CCR5 transfectants are used for assessing Ca$^{2+}$ mobilization in response to stimulation by the CCR5 ligands MIP-1α, MIP-1β, HCC-1(9-74) or RANTES. For the assay the cells are loaded with a Ca$^{2+}$-sensitive fluorochrome (Fluo3 or Fluo4). Ligand concentrations between 0.01-100 nM are used to induce Ca$^{2+}$ mobilization which is monitored in a fluorometer with appropriate settings.

To assess the activity of the compounds to be tested, a baseline fluorescence reading is taken after which the compounds at the desired concentration are added to the cells and fluorescence is further recorded for a certain time to assess whether compounds show agonistic effects. Next the agonist is added to the mixture and fluorescence monitored. The inhibition of Ca$^{2+}$ flux in the presence of the compounds to be tested is calculated from the inhibition of maximal fluorescence induced by the agonist. IC$_{50}$ values are calculated from dose-response curves obtained with the compounds. In this assay, compounds of formula I have an IC$_{50}$≦1 μM. For example, compounds of Examples 12 and 36 have IC$_{50}$ values of 29 nM and 8 nM, respectively.

c) CCR5 Functional Assay—Chemotaxis

CCR5 transfectants are generated In Jurkat T cells or the mouse pre B cell line L1.2. Migration of CCR5 transfectants is tested in transwell tissue chamber inserts system with the CCR5 agonist MIP-1α at concentrations of 1-100 nM. Cells migrated in response to the agonist compared to a buffer control are quantified in a flow cytometer. The compounds to be tested are added to the cells and the agonist compartments. IC$_{50}$ values are calculated from concentration-response curves obtained with the compounds In the presence of MIP-1α. In this assay, compounds of formula I have an IC$_{50}$≦1 μM.

d) Experiments performed in murine animal models show that vessel wall remodeling after experimental injury (e.g. induced by allotransplantation) is significantly inhibited in the absence of functional CCR5.

The compounds of formula I are, therefore, useful in the prevention and/or treatment of diseases or disorders mediated by interactions between chemokine receptors, e.g. CCR5, and their ligands, e.g. in transplantation, such as acute or chronic rejection of organ, tissue or cell allo- or xenografts or delayed graft function, autoimmune diseases, e.g. rheumatoid arthritis, systemic lupus erythematosus, Hashimoto's thyroidis, multiple sclerosis, myasthenia gravis, diabetes type I or II and the disorders associated therewith, vasculitis, pernicious anemia, Sjoegren syndrome, uveitis, psoriasis, alopecia areata and others, allergic diseases e.g. allergic asthma, atopic dermatitis, allergic rhinitis/conjnctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermattises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock and others, cancer, e.g. solid tumors or lymphatic cancer such as T cell lymphomas or T cell leukemias, metastasizing or anglogenesis, infectious diseases, e.g. toxic shock (e.g. superantigen induced), septic shock, adult respiratory distress syndrome or viral infections, e.g. AIDS. By transplantation is meant allo- or xeno grafts of e.g. cells, tissues or solid organs, for example pancreatic islets, stem cells, bone marrow, corneal tissue, neuronal tissue, heart, lung, combined heart-lung, kidney, liver, bowel, pabcreas, trachea or oesophagus. Chronic rejection is also named graft vessel diseases.

For the above uses the required dosage will of course vary depending on the mode of administration, the particular condition to be treated and the effect desired. In general, satisfactory results are indicated to be obtained systemically at daily dosages of from about 0.01 to 10 mg/kg per body weight. An indicated daily dosage in the larger mammal, e.g. humans, is in the range from about 0.5 mg to about 1000 mg, conveniently administered, for example, in divided doses up to four times a day or in retard form. Suitable unit dosage forms for oral administration comprise from ca. 1 to 500 mg active ingredient.

The compounds of formula I may be administered by any conventional route, in particular enterally, e.g. orally, e.g. in the form of tablets or capsules, or parenterally, e.g. In the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by interactions between chemokine receptors and their ligands, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I or a pharmaceutically acceptable salt thereof for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I or a pharmaceutically acceptable salt thereof in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

5. Use of a compound of formula I or a pharmaceutically acceptable salt thereof for preventing or treating a disorder or disease mediated by interactions between chemokine receptors and their ligands, e.g. such as indicated above.

6. Use of a compound of formula I or a pharmaceutically acceptable salt thereof for preventing or treating acute or chronic transplant rejection or inflammatory or autoimmune diseases, e.g. as indicated above.

7. Use of a compound of formula I or a pharmaceutically acceptable salt thereof for the preparation of a medicament for preventing or treating a disorder or disease mediated by interactions between chemokine receptors and their ligands, e.g. such as indicated above.

8. Use of a compound of formula I or a pharmaceutically acceptable salt thereof for the preparation of a medicament for preventing or treating acute or chronic transplant rejection or inflammatory or autoimmune diseases, e.g. as indicated above.

The compounds of formula I may be administered as the sole active ingredient or in conjunction with, e.g. as an adjuvant to, other drugs e.g. in immunosuppressive or immunomodulating regimens or other anti-inflammatory agents, e.g. for the treatment or prevention of allo- or xenograft acute or chronic rejection or inflammatory or autoimmune disorders, a chemotherapeutic agent or an anti-infective agent, e.g. an anti-viral agent such as e.g. an anti-retroviral agent or an antibiotic. For example, the compounds of formula I may be used in combination with a calcineurin inhibitor, e.g. cyclosporin A, ISA 247 or FK 506; a macrocyclic lactone having immunosuppressive properties, e.g. an mTOR inhibitor, e.g. rapamycin, 40-O-(2-hydroxyethyl)-rapamycin, CC1779 or ABT578; an ascomycin having immunosuppressive properties, e.g. ABT-281, ASM981, etc.; corticosteroids; cathepsin S inhibitors; cyclophosphamide; azathioprine; methotrexate; leflunomide; mizoribine; mycophenolic acid; mycophenolate mofetil; 15-deoxyspergualine or an immunosuppressive homologue, analogue or derivative thereof; a sphingosine-1-phosphate receptor agonist, e.g. FTY720 or Y-36018; monoclonal antibodies to leukocyte receptors, e.g., MHC, CD2, CD3, CD4, CD7, CD8, CD11a/CD18, CD25, CD27, CD28, CD40. CD45, CD58, CD80, CD86, CD137, ICOS, CD150 (SLAM), OX40, 4-1BB or to their ligands, e.g. CD154, or antagonists thereof; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA41 g (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists, e.g. natalizumab (ANTEGREN®); or antichemokine antibodies or antichemokine receptor antibodies or low molecular weight chemokine receptor antagonists, e.g. anti MCP-1 antibodies.

Where the compounds of formula I are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory, anti-infective or chemotherapeutic drug, e.g. as indicated above.

6. A pharmaceutical combination, e.g. a kit, comprising a) a first agent which is a CCR5 antagonist, e.g. a compound of formula I as disclosed herein, in free form or in pharmaceutically acceptable salt form, and b) at least one co-agent, e.g. an immunosuppressant, immunomodulatory, anti-inflammatory, anti-infective or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:

1. A compound of formula I

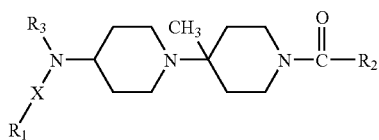

I wherein
1) $R_2$ is a residue of formula

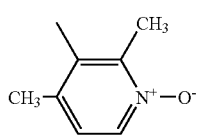

and
a) $R_1$ is thienyl, furyl, thiazolyl or 2-methyl-thiazolyl,
X is —$CH_2$—, and
$R_3$ is benzo[1,3]dioxol-yl or phenyl optionally mono-substituted by halogen,
or
b) $R_1$ is phenyl substituted by —$SO_2CH_3$ or CN
X is —$CH_2$—, and
$R_3$ is phenyl
or
c) $R_1$ is phenyl
X is a direct bond, and
$R_3$ is pyridyl,
or
2) $R_2$ is a residue of formula

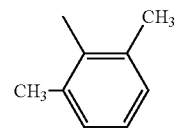

and
a) $R_1$ is pyridyl, phenyl optionally substituted by carboxy or $C_{1-4}$alkoxycarbonyl, 2-methylthiazolyl, indolyl or benzimidazol-2-yl,
$X_1$ is —$CH_2$— or —$CH_2$—$CH_2$—, and
$R_3$ is phenyl optionally substituted by Hal,
or
b) $R_1$ is phenyl
X is a direct bond
$R_3$ is pyridyl,
or
c) $R_1$ is 2-methyl-thiazolyl,
X is —$CH_2$—, and
$R_3$ is 1-methyl-indolyl
or
3) $R_2$ is a residue of formula

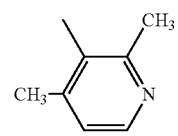

and
a) $R_1$ is 2-methyl-thiazolyl
X is —$CH_2$—, and
$R_3$ is phenyl substituted by halogen
or
b) $R_1$ is pyridyl
X is a direct bond, and
$R_3$ is phenyl
or
4) $R_2$ is a residue of formula

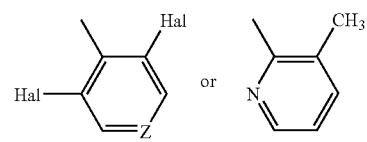

wherein
Hal is F or Cl,
Z is —C═ or —N═
and
a) $R_1$ is phenyl, X is a direct bond and $R_3$ is pyridyl or
b) $R_1$ is pyridyl, X is a direct bond and $R_3$ is phenyl.

2. A process for the preparation of a compound of formula I as defined in claim 1 which process comprises
a) amidating a compound of formula II

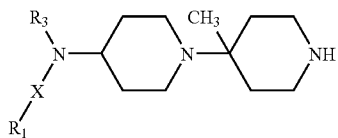

II wherein $R_1$, $R_3$ and X are as defined in claim 1 with a compound of formula III

   III wherein $R_2$ is as defined in claim 1, A is a leaving group, e.g. Cl or Br; or b) reacting a compound of formula IV

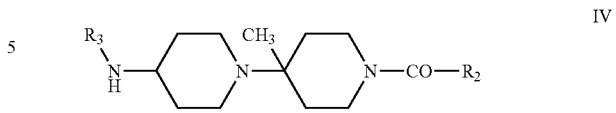

IV wherein $R_2$ and $R_3$ are as defined in claim 1, with a compound of formula V

   V wherein $R_1$ and X are as defined above;
and, where required, converting the resulting compound of formula I obtained in free form into the desired salt form, or vice versa.

3. A pharmaceutical composition comprising a compound of formula I as defined in claim 1 or a pharmaceutically acceptable salt thereof in association with a pharmaceutically acceptable diluent or carrier therefor.

* * * * *